US012606796B2

(12) United States Patent
Chumakov et al.

(10) Patent No.: US 12,606,796 B2
(45) Date of Patent: Apr. 21, 2026

(54) DELIVERY OF ONCOLYTIC VIRUSES USING DENDRITIC CELLS

(71) Applicant: SATOR Therapeutics LLC, Cleveland, OH (US)

(72) Inventors: Peter M. Chumakov, Solon, OH (US); Darya A. Berzhitskaya, Moscow (RU); Anastasia V. Lipatova, Moscow (RU); Stepan P. Chumakov, Moscow (RU); Natalia D. Tararova, Gates Mills, OH (US); Stephen A. Charles, Chagrin Falls, OH (US); Anton A. Komar, Gates Mills, OH (US)

(73) Assignee: SATOR THERAPEUTICS LLC, Cleveland, OH (US)

( * ) Notice: Subject to any disclaimer, the term of this patent is extended or adjusted under 35 U.S.C. 154(b) by 295 days.

(21) Appl. No.: 16/868,691

(22) Filed: May 7, 2020

(65) Prior Publication Data

US 2020/0352993 A1     Nov. 12, 2020

Related U.S. Application Data

(60) Provisional application No. 62/845,776, filed on May 9, 2019.

(51) Int. Cl.
| | |
|---|---|
| *C12N 5/0784* | (2010.01) |
| *A61K 35/768* | (2015.01) |
| *A61K 40/19* | (2025.01) |
| *A61K 40/24* | (2025.01) |
| *A61K 40/46* | (2025.01) |
| *A61P 35/00* | (2006.01) |
| *C12N 7/00* | (2006.01) |

(52) U.S. Cl.
CPC .......... *C12N 5/0639* (2013.01); *A61K 35/768* (2013.01); *A61K 40/19* (2025.01); *A61K 40/24* (2025.01); *A61K 40/46* (2025.01); *A61P 35/00* (2018.01); *C12N 7/00* (2013.01); *A61K 2239/31* (2023.05); *A61K 2239/38* (2023.05); *A61K 2239/47* (2023.05); *A61K 2239/50* (2023.05)

(58) Field of Classification Search
None
See application file for complete search history.

(56) References Cited

U.S. PATENT DOCUMENTS

| | | | |
|---|---|---|---|
| 2014/0087362 A1* | 3/2014 | Szalay | C07K 16/28 |
| | | | 435/5 |
| 2018/0085411 A1 | 3/2018 | Chumakov et al. | |

FOREIGN PATENT DOCUMENTS

| | | |
|---|---|---|
| CN | 101304761 A | 11/2008 |
| WO | 2013038066 A1 | 3/2013 |
| WO | 2018064134 A1 | 4/2018 |

OTHER PUBLICATIONS

Jammal, Sep. 2018, Ann. Transl. Med. vol. 6: 1-4.*
Comrie et al., 2015, J. Cell. Biol. vol. 208: 457-473.*
Willmon, 2009, Mol. Ther. vol. 17: 1667-1676.*
Montfort, 2007, J. Immunol. vol. 178: 3177-3185.*
Taylor, 2015, Immunol. Rev. vol. 268: 340-364.*
Goffard, 2013, Microbes and Infection vol. 15: 18-27.*
Dimitrov, 2017, Virology Journal, pp. 1-14.*
E. J. Ilett et al., "Dendritic cells and T cells deliver oncolytic reovirus for tumor killing despite pre-existing anti-viral immunity," Gene Therapy, vol. 16, No. 5, Mar. 12, 2009, pp. 689-699, GB.
E. J. Ilett et al., "Internalization of Oncolytic Reovirus by Human Dendritic Cell Carriers Protects the Virus from Neutralization," Clinical Cancer Research, vol. 17, No. 9, Mar. 9, 2011, pp. 2767-2776, US.
Robert A. Berkeley et al., "Antibody-Neutralized Reovirus Is Effective in Oncolytic Virotherapy," Cancer Immunology Research, vol. 6, No. 10, Oct. 1, 2018, pp. 1161-1173, US.
International Search Report from International Application No. PCT/US2020/031837 dated Aug. 17, 2020.
Chinese Office Action of Application No. 2020800347487 Dated Feb. 5, 2024.

* cited by examiner

*Primary Examiner* — Amy E Juedes
(74) *Attorney, Agent, or Firm* — Lippes Mathias LLP

(57) ABSTRACT

A versatile carrier system for systemic delivery of oncolytic viruses comprises dendritic cells having at least one oncolytic virus loaded therein. It is believed that the dendritic cells will protect the oncolytic virus(es) against neutralizing antibodies, can transport the oncolytic virus(es) to targeted tumor locations, and then deliver virions to the tumor locations.

7 Claims, 2 Drawing Sheets

DELIVERY OF ONCOLYTIC VIRUSES USING DENDRITIC CELLS

CROSS-REFERENCE TO RELATED APPLICATIONS

This application claims priority to U.S. Provisional Patent Application Ser. No. 62/845,776, filed on May 9, 2019, which is incorporated by reference in its entirety.

BACKGROUND

The present disclosure relates to methods for delivering oncolytic viruses to their targets. The oncolytic viruses are used for inhibiting or reducing cancerous cell proliferation and malignant tumor progression. Compositions for use in such methods are also disclosed.

Cancer is the abnormal growth of cells, which can create masses of tissue that can become malignant tumors or neoplasms. These formations can invade and destroy surrounding tissues, and may spread to other parts of the body forming metastases.

Treatment with oncolytic viruses is currently considered as a promising therapeutic approach that addresses many hurdles of conventional systemic cancer therapy. The main hurdles include high incidence of severe adverse effects of chemotherapeutic and targeted drugs and low efficiency of killing cancer initiating stem-like cells responsible for disease relapses. Current therapeutic protocols do not provide substantial increase in 5-year patients' survival if the disease is diagnosed at an advanced stage and cancer cells have spread through the body (i.e. metastasis has occurred). Existing approaches to immune therapy against cancer do not provide impressive outcomes, unless they are custom tailored to attack personalized features of the patient's tumor cells. However, these approaches are extremely expensive and are not sufficiently developed to secure reliable and reproducible responses. As a result, despite tremendous efforts and spent resources, overall cancer morbidity and mortality continues to increase in the USA and other developed countries.

Systemic delivery of oncolytic viruses into cancer patients is usually poorly efficient and does not ensure the entrance of a therapeutic virus into the tumor body that is sufficient to initiate virus replication in the tumor microenvironment and the induction of tumor cell lysis induced by virus replication and virus-stimulated immune mechanisms. Methods and compositions for efficient delivery of oncolytic viruses is desirable

BRIEF DESCRIPTION

Disclosed in various embodiments herein are compositions and methods for treating malignant diseases such as cancer. The present disclosure describes a versatile carrier system for systemic delivery of oncolytic viruses to distant tumors and their metastases based on patient derived or allogenic dendritic cells (DCs) obtained from peripheral blood monocytes. Oncolytic viruses are loaded into the dendritic cells and transported by the dendritic cells to a desired site or target.

It is contemplated that ex vivo infection of immature dendritic cells with different oncolytic viruses can provide protection for the viruses against neutralizing antibodies as the dendritic cells circulate through the body, and eventually result in the release of newly synthesized infection virions and death of the dendritic cells themselves. It is also contemplated that infected dendritic cells can transfer newly synthesized virions to virus-sensitive cancer cells in vitro, for example to syngeneic mouse tumors when the infected dendritic cells are injected into the tail vein of pre-immune mice, or to xenografts of human tumor cells grown as tumors in immune deficient nude mice.

It is believed that the presence of the oncolytic viruses may induce maturation of immature dendritic cells and induce their targeting to tumor locations. The delivery efficiency of the oncolytic viruses using dendritic cells may be substantially higher than when the viruses are merely injected intravenously (i.e. without the presence of the dendritic cells).

It is contemplated that in glioblastoma patients, dendritic cells may be able to deliver the viruses into brain tumors and provide durable therapeutic responses. In other words, the dendritic cells may transport the loaded viruses across the blood-brain barrier (BBB) into the brain tumors.

Proposed technology for cancer treatment described herein includes dendritic cells obtained from peripheral blood monocytes in vitro, loaded with oncolytic viruses ex vivo, and injected intravenously into the patient. Various schemes for simultaneous or sequential delivery of oncolytic viruses from a panel of therapeutic strains to cancer patients are also described.

Also disclosed herein are methods for monitoring virus replication in the patient's body following the delivery of the viruses by measuring virus genome sequences in the blood, for example through real-time polymerase chain reaction (PCR). An increase in the quantity of virus in the blood correlates with successful replication of the virus in the patient's cancer cells.

Also disclosed herein in several different embodiments are compositions, comprising: one or more dendritic cells; and at least one oncolytic virus loaded into the dendritic cell(s).

The dendritic cells may be autologous or allogeneic. The dendritic cells may be derived from peripheral blood monocytes.

The at least one oncolytic virus may be independently selected from a human enterovirus; a reovirus; a paramyxovirus; a rhabdovirus; a togavirus; a Herpes virus; a parvovirus; an adenovirus; a poxvirus; and a hybrid virus. The at least one oncolytic virus may be present in an amount of about $1 \times 10^4$ TCID50 to about $1 \times 10^{11}$ TCID50.

In some embodiments, the at least one oncolytic virus is a plurality of different viruses. The different viruses may differ in their host-cell surface receptor required for cell entry. The host-cell surface receptor required for cell entry may be CD155, integrin $\alpha 2 \beta 1$, integrin $\alpha V \beta 3$, integrin $\alpha V \beta 6$, ICAM-1, CD55, CXADR, FcRn, KREMEN1, CD46, JAM-1, PVRL1, PVRL4, CD150, L-SIGN, VLDVR, NRAMP2, sialic acid, PGSL-1 (aka CD162), SCARB2 (scavenger receptor class B, member 2), annexin II, DC-SIGN (dendritic cell-specific ICAM3-grabbing non-integrin), hPVR (human poliovirus receptor), CD34+, LDLR (Low-density lipoprotein receptor), JAM (Junctional Adhesion Molecule), or heparin sulfate.

The composition can be formulated to be administered orally, nasally, intravenously, intra-arterially, intradermally, subcutaneously, intramuscularly, intraperitoneally, intrapleurally, intravaginally, intraurethrally, intratumorally, intracranially, or intraspinally.

Also disclosed herein are methods for increasing the efficiency of loading an oncolytic virus into dendritic cells and/or monocytes (which act as cell carriers). Complexes of the oncolytic virus with a neutralizing antibody for that virus are more easily absorbed by dendritic cells and monocytes because such complexes can bind to Fc-receptors on the cell surface (the CD16A molecules) of the dendritic cells and monocytes. This binding to alternate receptors facilitates the endocytic entrance of the virus/antibody complex into the dendritic cells and monocytes, thereby enhancing the ex vivo loading of the oncolytic virus into the cell carriers. Thus, a complex is formed between an oncolytic virus and a neutralizing antibody for that virus. The complex is then brought into contact with a dendritic cell and/or monocyte, to be loaded into the dendritic cell or monocyte.

Also disclosed are methods of treating a cancer patient, comprising: administering to the patient a composition comprising dendritic cells and at least one oncolytic virus loaded therein.

The composition may be administered orally, nasally, intravenously, intra-arterially, intradermally, subcutaneously, intramuscularly, intraperitoneally, intrapleurally, intravaginally, intraurethrally, intratumorally, intracranially, or intraspinally.

Also disclosed are methods for monitoring virus replication in a patient following delivery, comprising: collecting blood samples at different time points; and measuring virus load in the blood samples.

Finally, also disclosed herein are various methods for treating a cancer patient, comprising: administering to the patient a first therapeutic composition comprising dendritic cells and at least a first oncolytic virus loaded therein; measuring loads of the first oncolytic virus in blood samples collected at different time points; and when the load of the first oncolytic virus reaches a threshold value, administering to the patient a second therapeutic composition comprising dendritic cells and at least a second oncolytic virus loaded therein, wherein the first oncolytic virus and the second oncolytic virus are different from each other.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
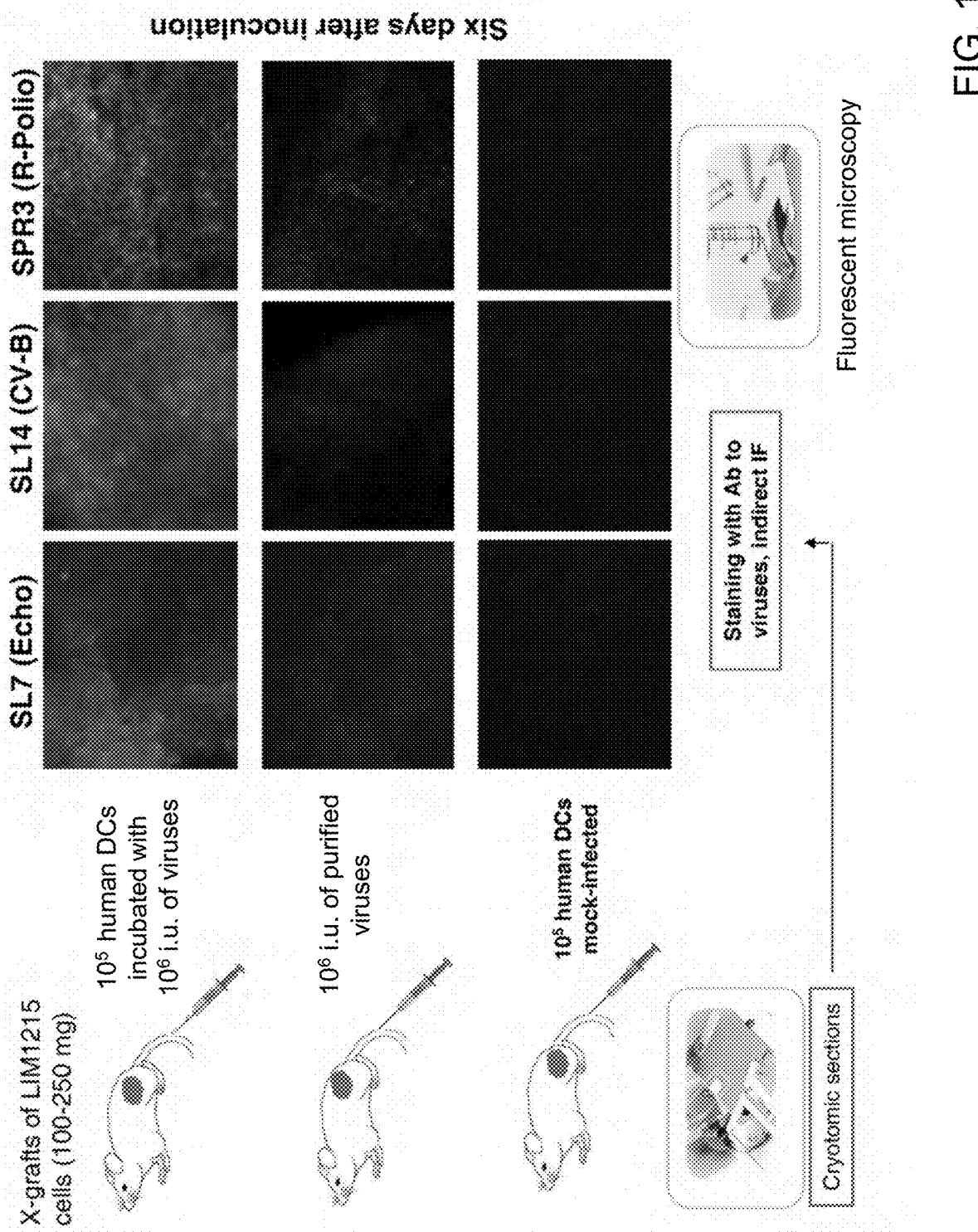
FIG. 1 is a drawing along with nine images, which illustrates experiments carried out on mice. Three different viruses were injected into mice using three different methods, as illustrated on the left-hand side. The results are shown on the right-hand side, which contains nine color images. From top to bottom, the rows are labeled as 10^5 human DCs incubated with 10^6 i.u. of viruses; 10^6 i.u. of purified viruses; and 10^5 human DCs mock-infected. From left to right, the columns are labeled as SL7 (Echo), SL14 (CV-B), and SPR3 (R-Polio). The images were taken six days after inoculation.

The present disclosure may be understood more readily by reference to the following detailed description of desired embodiments and the examples included therein. In the following specification and the claims which follow, reference will be made to a number of terms, which will be defined to have the following meanings.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The term "tumor" is used herein to refer both to a neoplasm that has formed a lump and to a neoplasm that has not formed a lump. The tumor can be malignant, or potentially malignant, or a secondary tumor.

The term "dendritic cell" refers to an antigen-presenting cell of the immune system, whose main function is to process antigen material and present it on the cell surface to T cells.

The term "oncolytic virus" refers to a virus having oncolytic properties. The oncolytic virus may be natural, improved by selection, or synthetically created.

The term "CV1" refers to a cell line derived from African green monkey kidneys (ATCC No. CCL-70). CV-1 cells exhibit fibroblast-like morphology, grow adherently to glass or plastic surfaces, and are negative for reverse transcriptase.

The term "TCID50" refers to 50% tissue culture infective dose, which is a measure of infectious virus titer. This endpoint dilution assay quantifies the amount of virus required to kill 50% of infected hosts or to produce a cytopathic effect in 50% of inoculated tissue culture cells.

The term "PFU" refers to plaque forming units in a virus sample, which is one measure of virus quantity. This assay is based on a microbiological method conducted in petri dishes or multi-well plates. Specifically, a confluent monolayer of host cells is infected with the virus at varying dilutions and covered with a semi-solid medium to prevent the virus infection from spreading indiscriminately. A viral plaque is formed when a virus infects a cell within the fixed cell monolayer. The virus-infected cell will lyse and spread the infection to adjacent cells where the infection-to-lysis cycle is repeated. The infected cell area will create a plaque (an area of infection surrounded by uninfected cells), which can be seen visually or with an optical microscope. Plaques are generally counted manually and the results, in combination with the dilution factor used to prepare the plate, are used to calculate the number of plaque forming units per sample unit volume (PFU/cell). The PFU/cell result represents the number of infective particles within the sample and is based on the assumption that each plaque formed is representative of one infective virus particle.

The term "identity" refers to the degree to which a pair of sequences (nucleotide or amino acid) has the same residue in the same location. Identity is measured by dividing the number of identical residues by the total number of residues (gaps are not counted) and multiplying the product by 100 to achieve a percentage. Thus, two copies of exactly the same sequence have 100% identity, but sequences that have deletions, additions, or substitutions may have a lower degree of identity. Those skilled in the art will recognize that several computer programs, such as those that employ algorithms such as BLAST, are available for determining sequence identity. BLAST nucleotide searches are performed with the NBLAST program, and BLAST protein searches are performed with the BLASTP program, using the default parameters of the respective programs.

Viral oncolysis operates through two mechanisms: (1) direct killing of cancer cells by selective infection and replication of viruses in malignant cells; and (2) the induction of systemic anti-tumor immunity that provides a long-lasting therapeutic effect even after clearing of the virus. Unlike chemotherapeutic drugs that have limited efficacy against the recurrent growth of tumors due to the resistance of cancer initiating stem cells, many oncolytic viruses are capable of infecting and killing cancer stem cells, thereby limiting probability of relapses. It is also noted that while normal cells display viral interference (a cell infected with a first virus display reduced susceptibility to being infected by a second virus), cancer cells may not.

The selectivity of viral replication in cancer cells is explained by better accessibility and exposure of cancer cells to viruses due to the chaotic organization of tumor tissue, compromised cell to cell contacts, and the presence of unengaged cell-surface molecules that act as virus entry receptors. However, the most significant hallmark of cancer cells that make them sensitive to viruses is compromised intrinsic anticancer defense mechanisms that involve deficiencies in type I interferon induction and in the response to interferon treatment. The interferon mechanisms are common early targets of inactivation during a malignant progression, making the cells vulnerable to viral replication and killing.

In addition to the direct virus mediated killing, oncolytic viruses stimulate both the innate immune system and the adaptive immune system, and overcome the immune suppressive effects of the tumor microenvironment. Virus replication inside the tumor is associated with the release of interferons, proinflammatory cytokines, and chemokines that attract components of the innate (NK-cells) and adaptive (dendritic cells (DCs) and T-lymphocytes) immune systems and that modify the tumor microenvironment. As a result, viral infection releases the suppressive and tumor promoting effects of myeloid-derived suppressive cells, and also assists in infiltration of the tumor with T-cells that makes the tumor more susceptible to immune checkpoint inhibitors.

Oncolytic viruses can be effective against tumors that are resistant to conventional cytotoxic and targeted drugs because they can kill apoptosis-resistant cells and their action mechanisms do not overlap with the action mechanisms of such drugs. Oncolytic viruses also do not discriminate between tumor cells and cancer initiating stem cells. This is why oncolytic viruses are capable of preventing tumor relapses even in such a grave disease as glioblastoma multiforme.

Although oncolytic viruses show great promise as therapeutics that have minimal or no side effects, and a high potential for providing sustained remission and even a cure for advanced metastatic malignancies, there are still some issues that need to be addressed to elaborate predictable and efficient therapeutic responses in the majority of patients and in different forms of cancer.

One issue is the unpredictable response of patients to therapy with oncolytic viruses. When treated with a single oncolytic virus, some patients (10-30%) demonstrate positive responses of various degrees, but others may not respond at all. This issue can be resolved by identifying another oncolytic virus strain to which the patient will respond. For example, multiple oncolytic viruses can be administered concurrently, with the expectation that the patient will respond to at least one of the administered viruses. The viruses should differ from each other in at least one respect.

Another serious issue relates to modes of administration of oncolytic viruses. A systemic administration (the intravenous or intramuscular injection of a virus preparation) is far from efficient, because even without a preexisting antiviral immunity as low as >0.001% of the administered virions may reach the tumor, while the vast majority of the input dose is taken up from the circulation by scavenger cells in the blood or reticuloendothelial organs. Complement proteins can also compromise virus delivery to tumors. Viruses do not survive in the bloodstream longer than a few minutes. Besides, viruses have very limited ability for extravasation into the tumor mass because of high interstitial fluid pressure within the tumor, which further hinders their delivery. By increasing virus dose, the innate barriers can ultimately be overwhelmed. However, the adaptive immune response to the introduced virus later represents a critical obstacle to systemic administration of virotherapeutics. Antiviral neutralizing antibodies appear as early as 4 days after the initial administration, and may reach a maximum 2-3 weeks later. To overcome the effect of virus neutralization in circulation, a substantial escalation of dose is required that makes the treatment much more expensive and still does not ensure acceptable outcomes.

To protect viruses from their elimination in the bloodstream en route to tumor sites, a carrier system capable of time-dependent release and of preferentially targeted delivery is desired. Cell-based delivery systems for oncolytic viruses are widely considered to circumvent anti-viral immunity. Such delivery systems are based on cells that are either permissive for virus replication and can amplify the virus while being in circulation, or mechanically absorb and protect the virus and deliver it to tumor sites without replication. Virus introduction with the systems includes ex vivo virus loading, intravenous inoculation of infected cells and finally, virus release in tumor sites.

Cell-based carriers useful for systemic delivery of oncolytic viruses desirably have certain properties. The carrier should be easy to infect with the virus, and should permit virus replication. The carrier should be able to deliver viruses to specific tumor locations, for example by homing in on locations of inflammation or neovascularization that are characteristic of tumors. The carrier should not be too large, as large cells may lodge in the small capillary beds of the lungs or liver, preventing further circulation, and a smaller size may permit the carrier to migrate through endothelial walls into the tumor microenvironment. The carrier itself may also possess intrinsic antitumor activity, which could potentially produce synergistic therapeutic effects.

In the present disclosure, dendritic cells (DCs) are used as a cell-based virus carrier to transport oncolytic viruses and deliver them to tumor locations. Dendritic cells are specialized antigen-presenting cells that bridge the innate and adaptive immune systems by identifying pathogens, non-self components, and neoantigens. Due to their high endocytic activity and the presence of specialized receptors recognizing diverse pathogen-associated molecular patterns (PAMPs), dendritic cells avidly absorb bacteria and viruses and present their components to T-cells. While taking up viruses, dendritic cells are capable of limited replication of some viruses, and the infection can modulate the physiology of dendritic cells. It has been found that dendritic cells permit replication of diverse arrays of viruses, including adenoviruses, reoviruses, enteroviruses, vaccinia virus, Newcastle disease virus (NDV), vesicular stomatitis virus (VSV), Sendai virus, measles virus, Japanese encephalitis virus, Sindbis virus, Lassa virus, and Dengue virus. Many viruses can penetrate dendritic cells though a specialized pathogen-sensing receptor, DC-SIGN (aka CD209). However, other routes of virus entry to dendritic cells may also exist.

As dendritic cells can support replication of a rather diverse array of virus strains, they represent an attractive system for the development of a versatile delivery vehicle system for different oncolytic virus strains. The system would be particularly valuable for systemic administration of personalized panels of oncolytic virus strains.

The present disclosure contemplates the use of dendritic cells (DCs) for ex vivo loading of different oncolytic viruses, their intravenous introduction to experimental animals and cancer patients, and successful therapeutic outcomes of such route of therapeutic administration. In particular embodiments, the dendritic cells are derived from immature monocytes, and are known as monocyte-derived dendritic cells (MDDCs). Immature dendritic cells constantly sample the surrounding environment for pathogens such as viruses, which eases uptake of the oncolytic virus(es). MDDCs can be generated in vitro from peripheral blood mononuclear cells (PBMCs). Alternatively, the dendritic cells can be isolated from blood using enrichment techniques known in the art. As a result, the dendritic cells can be allogeneic or autologous.

The present disclosure also describes methods for the enhancement of ex vivo loading of CD16-positive MDDCs and/or monocytes by the addition of neutralizing antibodies specific to the chosen oncolytic virus strain. The virus-antibody complexes attach to CD16A receptors on the MDDCs or monocytes, through the affinity between the Fc-domain of antibodies and the Fc-binding domain of Fc-gamma-RIII (CD16A) protein.

The oncolytic virus(es) used in conjunction with the dendritic cells are non-pathogenic human viruses with oncolytic activity, and include panels of combinations of different oncolytic viruses. The viruses used in combination together should differ in their antigenic structures, so that they do not cross-neutralize with antibodies. The viruses can display overlapping requirements for host-cell specific factors, but should not be identical. These requirements may include but are not limited to, the host-cell surface receptor used for virus-entry receptors, components of the antiviral innate immune system, etc. The viruses can be used sequentially or simultaneously, in combination of two, three or more different viruses. Examples of oncolytic virus combinations for sequential and simultaneous applications are disclosed.

In this regard, different strains of virus serotypes rely on different host-cell surface protein receptors to gain entry to cells. For example, Echovirus 1 relies on integrin $\alpha2\beta1$ (alpha-2-beta-1); Echoviruses 7, 12, and 21 on CD55 (also known as DAF); Coxsackieviruses A7 and A9 on Integrin $\alpha V\beta3$, Integrin $\alpha V\beta6$, ICAM-1, and CD55; Coxsackieviruses B1-B6 on CXADR (also known as Coxsackievirus and adenovirus receptor or CAR); Coxsackieviruses B1, B3 and B5 on CD55; Edmonston strains of measles virus rely on CD46; canine distemper virus relies on nectin 4; and orthoreoviruses rely on JAM-1. In addition, many members of the Enterovirus B species, including Echoviruses 1, 3, 6, 7, 9, 11, 13, 14, 25, 26, and 30, Enterovirus B85 and Coxsackievirus A9 rely on the FcRn receptor protein for cell entry. FcRn is an MHC class I-like protein consisting of a heavy a chain encoded by the FCGRT gene, and a light beta2-microglobulin ($\beta2$m) chain encoded by the B2M gene. Members of the Enterovirus A species, including Coxsackievirus A10, use the product of the KREMEN1 gene as the receptor for cell entry. It is contemplated that one method by which cancer cells resist infection by viruses is by changing the expression and cell-surface exposure of receptors. There may be other factors that affect the efficiency of a virus to infect a particular cell type. As a result, the use of sequential viruses should allow for more extended courses of virotherapy, avoiding diminished efficiency of a single oncolytic virus strain because of the development of neutralizing antibodies against a particular virus or selection of cancer cells that are resistant to the particular virus (e.g. by changing the expression of the host-cell surface receptor needed by the particular virus).

In one broad aspect, then, it is contemplated that the oncolytic viruses can be used sequentially. Generally, a first therapeutic composition containing an effective amount of dendritic cells loaded with at least a first oncolytic virus is administered to the patient for a first time period. Then, a second therapeutic composition containing an effective amount of dendritic cells loaded with at least a second oncolytic virus is administered to the patient for a second time period. The therapeutic compositions are administered sequentially. In other words, the first therapeutic composition is administered, then the administration of the first therapeutic composition is stopped and the second therapeutic composition is administered. Put another way, a panel of therapeutic compositions is administered sequentially to the patient, i.e. one composition at a time but multiple compositions in a row. Each composition comprises dendritic cells loaded with one or more different oncolytic viruses.

The compositions containing the oncolytic viruses can be used/administered sequentially, each for a given time interval. In particular embodiments, the interval for which a given composition is used is between about 48 hours to about 4 weeks. In other embodiments, the interval is from about one week to about six weeks. In other words, the second composition is administered after the first composition is administered for this time period. It is noted that the compositions can be administered multiple times during this time period, as well as in multiple locations on the patient's body. In such cases, then, the time period for a given composition should be determined by the time between the first administration and the last administration of the given composition.

In addition, there may be an intermediate interval between the administration of the first and second compositions, which is the time between the last administration of the first composition and the first administration of the second composition. This intermediate "pause" or "rest" interval may be as few as 240 hours (10 days), and generally should be at least 336 hours (14 days), and may be as long as 672 hours (28 days). For example, if the first composition is administered on days 1 and 7, and the second composition is then administered on day 21, there is a rest interval of about 13 days (days 8-20). It is contemplated that no oncolytic viruses are administered to the patient during this intermediate interval.

The first and second oncolytic viruses should be different from each other, for example in the host-cell surface receptor required for cell entry. More specifically, the host-cell surface receptor required for cell entry oncolytic viruses can be selected from PVR (CD155), integrin α2β1 (alpha-2-beta-1), integrin αVβ3 (alpha-V-beta-3), integrin αVβ6 (alpha-V-beta-6), ICAM-1, CD55 (aka DAF), CXADR (aka CAR), FcRn, KREMEN1, CD46, JAM-1, PVRL1, PVRL4, SLAM (CD150), L-SIGN, VLDVR, NRAMP2, sialic acid, PGSL-1 (aka CD162), SCARB2 (scavenger receptor class B, member 2), annexin II, DC-SIGN (dendritic cell-specific ICAM3-grabbing non-integrin), hPVR (human poliovirus receptor), CD34+, LDLR (Low-density lipoprotein receptor), JAM (Junctional Adhesion Molecule), or heparan sulfate. The first and second oncolytic viruses could also be different from each other by targeting different specific defects in a particular type of cancer cells, such as mutations within proto-oncogenes, or different tumor suppressor genes, or different changes in programmed cell death pathways, alterations within various components of antiviral innate immunity mechanisms responsible for pathogens sensing and the development of antiviral resistance in response to interferon, etc. These defects in cancer cells may confer selective replication and cell killing advantages to some viruses, while being obsolete to others. The sequential application of different oncolytic viruses increases incidence of positive therapeutic responses among patients.

As an alternative, the simultaneous use of several oncolytic virus strains can be considered. Put another way, the first therapeutic composition and/or the second therapeutic composition can comprise a plurality of different oncolytic viruses. Two to four different oncolytic virus strains may be loaded into dendritic cells in each therapeutic composition of the panel. The virus strains in each therapeutic composition should be chosen based on their complementing spectrums toward different types of malignant cells. The approach has the following advantages and benefits for the patient:

(i) better chances for positive match of an active oncolytic virus capable of destroying the patient's tumor;

(ii) lower probability of selection of tumor cells that are resistant to a particular virus that uses a specific mechanism of cell entry and replication; and (iii) lower probability of complications because of an individual sensitivity of the patient to an oncolytic virus.

Viruses in the therapeutic compositions should induce the production of interferons that protect the patient from potential virus pathogens. Cancer cells are generally less sensitive to interferon, which underlies the specificity of oncolytic virus action against malignant cells. The use of mixtures of viruses would also permit the use of (a) conditionally pathogenic viruses or (b) custom-selected variants of oncolytic viruses that have not undergone extensive safety trials. The latter is particularly important for personalized approaches to oncolytic virus therapy. A conditionally (or potentially) pathogenic virus originates from rapidly evolving non-pathogenic strains that form heterogeneous quasi-species, some variations of which may acquire pathogenic properties, especially in immunocompromized individuals.

The oncolytic viruses used in the methods and compositions disclosed herein can be of the family of Picornaviridae, Reoviridae, Paramyxoviridae, Togaviridae, Rhabdoviridae, Adenoviridae, Herpesviridae, Parvoviridae, Poxviridae. In particular embodiments, the oncolytic viruses can be independently selected from a human echovirus; Coxsackievirus; a Sabin strain of poliovirus; human reovirus type 1, 2, or 3; a measles virus; a mumps virus; a Newcastle disease virus; a Sendai virus; a Vaccinia virus; a canine distemper virus; Maraba virus; or vesicular stomatitis virus (VSV).

Specific viruses contemplated for use include echoviruses 1-7, 9, 11-27, 29-33; Coxsackieviruses A1-A22 and A24; Coxsackieviruses B1-136; poliovirus Sabin strains 1-3; measles virus vaccine strains Edmonston, Moraten, Zagreb, AIK-C, Rubeovax, Schwarz, CAM-70, Changchun-47, Leningrad-4 and Shanghai-191; mumps virus vaccine strains Jeryl-Lynn, RIT 4385, Leningrad-3, Leningrad-Zagreb, Urabe Am9, and S79; Newcastle disease virus strains La Sota, B1, V4, VG-GA, Ulster 2C, Fuller, R2B, Mukteswar, and Komarov; Sendai virus strains Cantell, Fushimi, Z, and Hamamatsu; Vaccinia virus strains Lister, Dryvax, EM63, ACAM2000, Ankara, and LC16m8.

Other oncolytic viruses that might be useful in the therapeutic compositions of the present disclosure include small RNA viruses like reoviruses and enteroviruses; small DNA parvoviruses; medium-sized DNA adenoviruses; large enveloped DNA herpes viruses; large and complex DNA poxviruses; or medium and large enveloped single-strand RNA paramyxoviruses, rhabdoviruses, alfaviruses, and togaviruses. Each of these viral platforms have their specific advantages and drawbacks, somewhat different mechanisms of oncolytic action, spreading in the body, preferential routes of administration, etc.

The dendritic cells can be loaded/infected with the oncolytic virus(es) either as immature monocytes, immature dendritic cells, or as mature dendritic cells. The dosage of each virus in the therapeutic oncolytic composition is from about $1 \times 10^4$ ($10^4$) TCID50 per milliliter (mL) to about $1 \times 10^{11}$ ($10^{11}$) TCID50 per milliliter.

As previously mentioned, loading efficiency of the dendritic cells can be increased (i.e. loaded more quickly, or higher amount of loading) by forming a complex of an oncolytic virus with a neutralizing antibody for that oncolytic virus, and then loading the complex into the dendritic cells. This can be done ex vivo as a two-step process (first form the complex, then contact the dendritic cells with the complex) or as a one-step process (where the oncolytic virus, the neutralizing antibody, and the dendritic cells are all contacted/mixed together). Viral entry of the complex into the dendritic cells occurs via the Fc-receptor (always present on the cell surface of the dendritic cell) instead of the virus-specific receptor (which may be absent from the cell surface for some viruses). This is typically done in solution. Methods for preparing an antibody that neutralizes a given virus are known in the art.

It is contemplated that the therapeutic compositions of the present disclosure (comprising one or more oncolytic viruses loaded into dendritic cells) can be administered via an intratumoral, oral, nasal, intravenous, intra-arterial, sub-cutaneous, intradermal, intramuscular, intraperitoneal, intrapleural, intravaginal, intraurethral, intraspinal and intracranial route, depending on the malignant disease and particular virus strains used. The dendritic cells act as a carrier for the oncolytic viruses, with the therapeutic compositions containing a pharmaceutically effective amount of the oncolytic virus(es).

The therapeutic composition may be provided in the dosage form of a powder, capsule, tablet, granule, injection, solution, suspension, or emulsion. In some embodiments, the therapeutic composition also includes a carrier for delivering the virus-loaded dendritic cells. Examples of pharmaceutically acceptable carriers include liquid carriers like water, oil, and alcohols, in which the virus-loaded dendritic cells can be dissolved or suspended.

The therapeutic composition may also include excipients if desired, and possibly depending on the dosage form. Particular excipients may include buffering agents, surfactants, preservative agents, bulking agents, polymers, and stabilizers. Buffering agents are used to control the pH of the composition. Surfactants are used to stabilize proteins, inhibit protein aggregation, inhibit protein adsorption to surfaces, and assist in protein refolding. Exemplary surfactants include Tween 80, Tween 20, Brij 35, Triton X-10, Pluronic F127, and sodium dodecyl sulfate. Preservatives are used to prevent microbial growth. Examples of preservatives include benzyl alcohol, m-cresol, and phenol. Bulking agents are used to add bulk. Hydrophilic polymers such as dextran, hydroxyl ethyl starch, polyethylene glycols, and gelatin can be used to stabilize proteins. Polymers with nonpolar moieties such as polyethylene glycol can also be used as surfactants. Protein stabilizers can include polyols, sugars, amino acids, amines, and salts. Suitable sugars include sucrose and trehalose. Amino acids include histidine, arginine, glycine, methionine, proline, lysine, glutamic acid, and mixtures thereof. Proteins like human serum albumin can also competitively adsorb to surfaces and reduce aggregation. It should be noted that particular molecules can serve multiple purposes. For example, histidine can act as a buffering agent and an antioxidant. Glycine can be used as a buffering agent and as a bulking agent.

Successful delivery of oncolytic virus to tumor locations can be determined by the fact that if the virus reaches virus-sensitive tumor tissue, the patient responds with a fever which commonly lasts for 4-7 days. Such prolonged fever is common with dendritic cell delivery, and rare when intravenous (IV) administration of the virus is used instead. Also contemplated herein are protocols for monitoring virus presence in the blood at different time points following administration. A real-time PCR-based quantitative test can be used. In the absence of information on which particular virus strain is most effective in a given patient, two different viruses loaded on dendritic cells are simultaneously introduced. Blood samples are then collected at different time points, and the virus load is measured. An increase in virus load indicates that the virus can successfully replicate in the patient's body. The relative replication capacity of the two viruses that are introduced simultaneously can then be compared. This test is also valuable with subsequent virus introductions, because it can be used to detect when one virus stops replicating. This indicates that it is time to introduce a different virus strain to the patient.

The present disclosure is further illustrated in the following non-limiting working examples, it being understood that these examples are intended to be illustrative only and that the disclosure is not intended to be limited to the materials, conditions, process parameters and the like recited herein.

EXAMPLES

Example 1: Obtaining Dendritic Cells from Human Peripheral Blood

Solutions and Media:

RPMI-1640 cell culture media, supplemented with 10% fetal bovine serum.

RPMI-1640 cell culture media, supplemented with 2 mM L-glutamine, 25 mM HEPES, 10% fetal bovine serum; PBS-complete;

PBS buffer with 10 mM HEPES, 0.5% BSA and 1% glucose, pH 7.4.

Monocyte Isolation:

Pour into a 50 mL test tube 15 mL Ficoll® (density=1.077). Ficoll is the trademark for a neutral, highly branched, high-mass, hydrophilic polysaccharide which dissolves readily in aqueous solutions. Ficoll radii range from 2-7 nm. It is prepared by reaction of the polysaccharide with epichlorohydrin.

Collect blood into a vacutainer (we used 2 9 ml vacutainers with K3EDTA, lot #A15104KD). Total amount of blood required for the isolation is 30 mL. Do not chill the blood, use as fresh as possible (3-4 hours is OK). Bring the blood with PBS-complete to 200 m L.

Place 15 mL of Ficoll® solution (density=1.077) into a 50 mL sterile polypropylene conic centrifuge tube and overlay with 25 mL of the diluted blood. Centrifuge at 500 gravities for 30 minutes, without break. Collect the mononuclear cells fraction with a 10 mL dispenser and place into a 50 mL tube with 40 mL of PBS-complete.

Wash twice by resuspending in 45 mL PBS-complete. Centrifuge at 300 gravities for 10 minutes, discard the supernatant. Resuspend the combined pellets in 20 mL of RPMI-10 medium, pour into two 10 cm cell culture dishes.

Incubate for 1.5 hours at 37° C. in a $CO_2$ incubator. During this time, monocytes should attach. Remove unattached cells by gentle washing (4-5×) with 10 mL of PBS-complete, control the process under an inverted microscope.

Differentiation of Monocytes to Dendritic Cells.

Incubate monocytes in RPMI-10 medium supplemented with 500 U/mL IL-4 and 800 U/mL GM-CSF for five days. This should produce approximately $2 \times 10^7$ immature dendritic cells.

Infection of Immature Dendritic Cells with Oncolytic Viruses:

Dendritic cells are collected in 10 mL RPMI medium supplemented with 2% FBS and incubated in suspension with the virus (MOI=10, that is 10 infection units of the virus to one dendritic cell) for 3-4 hours at 37° C. Dendritic cells are then washed in PBS without serum by centrifugation at 300 gravities for 10 minutes, and suspended in 20 mL of 1:1 F12 medium:PBS (no antibiotics and serum) and kept at ~10° C. At this stage, the cell should be quickly transported to the patient (maximum time up to 5-6 hours) and injected intravenously. The injection volume is 20 mL.

Some alternative protocols can be taken from https://www.ncbi.nlm.nih.gov/pmc/articles/PMC4559332/.

Expected Manifestations.

After approximately 30-36 hours, patient temperature should start rising. The magnitude of temperature rise is very much individual. Antipyretics should be kept ready for addressing the fever. Temperature rises can last for 4-6 days. Local sensations may also be felt. On instrumental examination, signs of pseudo progression may be observed, due to local inflammation during virus infection.

Optimal Time Schedule for Dendritic Preparation and Injection.

Blood collection and dendritic cell preparation will take approximately five days before being ready for injection. Manifestations should typically subside in 6-7 days after the injection. The next blood collection and dendritic cell preparation is recommended to take place 7-10 days after the previous injection.

Advice for Choosing Viruses.

First choice. Poliovirus 1 (vaccine Sabine strain) plus Coxsackie B5 (LEV14 strain);

Repeat injections until manifestations disappear (2-3 cycles)

Second choice. NDV (H-strain) plus Coxsackievirus A7 (2-3 cycles).

Example 2: Ex Vivo Loading, Cellular Model

Human dendritic cells efficiently transfer oncolytic viruses to virus-sensitive cells. $2\times10^5$ dendritic cells were incubated with $2\times10^6$ infectious units (i.u.) of viruses for 2 hours at 37° C. The dendritic cells were then washed 3× with phosphate buffered saline (PBS) and incubated with neutralizing antibodies to the viruses for 1 hour. Serial dilutions of infected dendritic cells were then added to virus-sensitive cells and the efficiency of virus transfer was measured by counting the number of infected viral particles per the sensitive cell (reflected as MOI (multiplicity of infection) units). The percentage of infected cells varied with different virus strains, but on average was ~50% for many viruses used. See Table A below.

TABLE A

| Virus strain | % infected dendritic cells (MOI = 10 i.u./cell) |
|---|---|
| SL7 (Echovirus) | 25-50 |
| SL14 (Coxsackie B-like) | 15-20 |
| SPR3 (recombinant Poliovirus III) | 25-50 |
| SL7 (Coxsackievirus A-like) | 30-75 |
| SL4 (Echovirus) | 15-30 |
| SR2 (Orthoreovirus) | 7-15 |
| SSM (Sendai virus) | 60-75 |
| SNH (NDV) | 60-75 |
| SVRG (recombinant Vaccinia) | 50-90 |

Human dendritic cells and monocytes are loaded more efficiently with oncolytic viruses ex vivo in the presence of neutralizing antibodies specific for the chosen virus. $2\times10^5$ dendritic cells (or $2\times10^5$ monocytes) were incubated with $2\times10^6$ infectious units (i.u.) of viruses for two hours in the presence of 10 neutralizing doses of antibodies specific for the viruses at 37° C. The dendritic cells were washed 3× with phosphate buffered saline (PBS) and incubated with neutralizing antibodies to the viruses for one hour. Serial dilutions of infected dendritic cells were then added to virus-sensitive cells, and the efficiency of virus transfer was measured by counting the number of infected viral particles per the sensitive cell (reflected as MOI (multiplicity of infection) units). The loading of cells varied with different virus strains, but were not less, but up to 1.5-fold more efficient than if carried out without the virus-neutralizing antibodies.

Example 3: Mouse Xenograft Model

The efficiency of virus delivery via dendritic cells to tumors was further tested in a mouse xenograft model. Human LIM1215 colon carcinoma cells were subcutaneously introduced into athymic nude mice. Each mouse was injected subcutaneously with $2\text{-}10\times10^6$ LIM1215 colon carcinoma cells. When tumor volume reached approximately 0.1 to 0.15 mL, mice were injected intravenously with $10^5$ human dendritic cells that were infected with $10^6$ i.u. of three different viruses (Echo, CV-B, R-polio). After six days, the virus spread was assessed using immunostaining of tumor tissues with virus-specific antibodies. Control mice were injected with either $10^5$ human dendritic cells (mock-infected) or $10^6$ i.u. of purified viruses. FIG. 1 shows the results based on each method of virus delivery to the tumor. The highest efficiency was attained using the dendritic cell based approach, as evident by the increased staining of tumor tissues (top row) for all three of the tested viruses.

Example 4: Injection into Human

Figure 2:
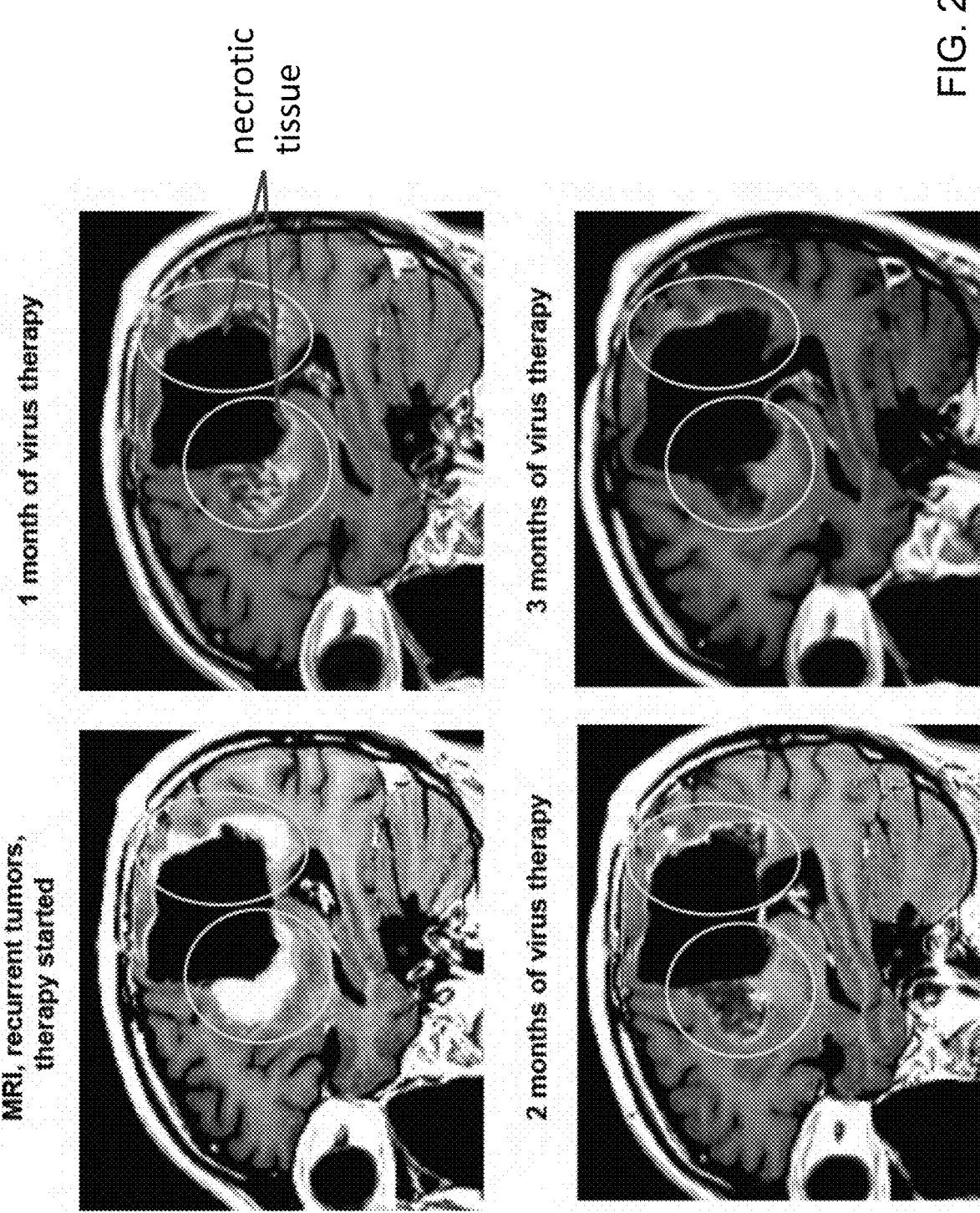
FIG. 2 is a set of four MRI images. The upper left MRI image was taken at the start of viral therapy. The upper right MRI image was taken after 1 month of viral therapy. The lower left MRI image was taken after 2 months of viral therapy. The lower right MRI image was taken after 3 months of viral therapy. The circles in the images indicate necrotic tissue.

The patient was a 41 year-old male diagnosed with Glioblastoma (stage IV). The patient underwent osteoplastic craniotomy in the right temporo-parietal region, resulting in macroscopic removal of the tumor. The patient further underwent radiation therapy, and four courses of chemotherapy (temozolomide). The tumor relapsed (see FIG. 2, left MRI, circled areas). At this point in time virus therapy was started, which used the patient's own dendritic cells. Dendritic cells were loaded ex vivo with two different virus strains and intravenously injected (~$5\times10^6$ virus-loaded dendritic cells were used) biweekly into the patient. The general condition of the patient improved rapidly within 1 month (see FIG. 2, center MRI). The MRI scan revealed a reduction in tumor size, as evident by the reduced accumulation of contrast. Two months after the start of the virus treatment, there was no progression of the disease, and the patient's condition was stable (see FIG. 2, right MRI). The tiny remaining enhanced area on the MR image represents necrotic tissue.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of treating a cancer patient, comprising:
administering to the patient a composition comprising dendritic cells loaded therein with a complex of (a) an oncolytic virus and (b) a neutralizing antibody for the oncolytic virus;
wherein the at least one oncolytic virus is vaccinia.

2. The method of claim 1, wherein the composition is administered orally, nasally, intravenously, intra-arterially, intradermally, subcutaneously, intramuscularly, intraperitoneally, intrapleurally, intravaginally, intraurethrally, intratumorally, intracranially, or intraspinally.

3. A method for treating a cancer patient, comprising:

administering to the patient a first therapeutic composition comprising dendritic cells loaded therein with a complex of (a) a first oncolytic virus and (b) a neutralizing antibody for the first oncolytic virus;

measuring loads of the first oncolytic virus in blood samples collected at different time points; and when the load of the first oncolytic virus reaches a threshold value, administering to the patient a second therapeutic composition comprising dendritic cells loaded therein with a complex of (a) a second oncolytic virus and (b) a neutralizing antibody for the second oncolytic virus, wherein the first oncolytic virus and the second oncolytic virus are different from each other; and wherein either the first oncolytic virus or the second oncolytic virus is vaccinia.

4. The method of claim 3, wherein the dendritic cells are autologous or allogeneic, or wherein the dendritic cells are derived from peripheral blood monocytes.

5. The method of claim 3, wherein the first and second oncolytic viruses are independently present in an amount of about $1 \times 10^4$ TCID50 to about $1 \times 10^{11}$ TCID50.

16

6. The method of claim 3, wherein the first and second oncolytic viruses differ in their host-cell surface receptor required for cell entry; and wherein the host-cell surface receptor required for cell entry is CD155, integrin $\alpha 2\beta 1$, integrin $\alpha V\beta 3$, integrin $\alpha V\beta 6$, ICAM-1, CD55, CXADR, FcRn, KREMEN1, CD46, JAM-1, PVRL1, PVRL4, CD150, L-SIGN, VLDVR, NRAMP2, sialic acid, PGSL-1 (aka CD162), SCARB2 (scavenger receptor class B, member 2), annexin II, DC-SIGN (dendritic cell-specific ICAM3-grabbing non-integrin), hPVR (human poliovirus receptor), CD34+, LDLR (Low-density lipoprotein receptor), JAM (Junctional Adhesion Molecule), or heparin sulfate.

7. The method of claim 3, wherein the first and second therapeutic compositions are administered orally, nasally, intravenously, intra-arterially, intradermally, subcutaneously, intramuscularly, intraperitoneally, intrapleurally intravaginally, intraurethrally, intratumorally, intracranially, or intraspinally.

* * * * *